US006420355B2

(12) United States Patent
Richter et al.

(10) Patent No.: US 6,420,355 B2
(45) Date of Patent: Jul. 16, 2002

(54) PHARMACEUTICAL COMPOSITIONS CONTAINING CYCLOSPORINS

(75) Inventors: Friedrich Richter, Grenzach-Wyhlen (DE); Jacky Vonderscher, Riedisheim (FR)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/826,719

(22) Filed: Apr. 5, 2001

Related U.S. Application Data

(63) Continuation of application No. 09/444,974, filed on Nov. 22, 1999, now abandoned, which is a continuation of application No. 09/174,904, filed on Oct. 19, 1998, now abandoned, which is a continuation of application No. 08/971,432, filed on Nov. 17, 1997, now abandoned, which is a continuation of application No. 08/570,273, filed on Dec. 11, 1995, now abandoned, which is a continuation of application No. 08/126,946, filed on Sep. 24, 1993, now abandoned.

(30) Foreign Application Priority Data

| Sep. 25, 1992 | (GB) | 9220245 |
|---|---|---|
| Sep. 25, 1992 | (GB) | 9220246 |
| Sep. 25, 1992 | (GB) | 9220247 |

(51) Int. Cl.$^7$ .......................................... A61K 31/545
(52) U.S. Cl. ..................... 514/200; 514/937; 514/951
(58) Field of Search ................................ 514/200, 937, 514/951

(56) References Cited

U.S. PATENT DOCUMENTS

| 3,288,824 A | 11/1966 | Mahler et al. ............ 260/410.6 |
|---|---|---|
| 3,813,345 A | 5/1974 | Urton ......................... 252/312 |
| 3,954,967 A | 5/1976 | Urton ........................... 424/78 |
| 4,073,943 A | 2/1978 | Wretlind et al. ............. 424/358 |
| 4,146,499 A | 3/1979 | Rosano ....................... 252/186 |
| 4,156,719 A | 5/1979 | Sezaki et al. ............... 424/177 |
| 4,388,307 A | 6/1983 | Cavanak |
| 4,482,576 A | 11/1984 | Boot et al. .................. 426/603 |
| 4,567,161 A | 1/1986 | Posanski et al. ............ 424/199 |
| 4,652,406 A | 3/1987 | Lepper et al. ............ 260/410.9 |
| 4,695,450 A | 9/1987 | Bauer et al. ................ 424/168 |
| 4,719,239 A | 1/1988 | Muller et al. ............... 514/785 |
| 4,794,000 A | 12/1988 | Ecanow ....................... 424/457 |
| 4,797,272 A | 1/1989 | Linn et al. .................... 424/59 |
| 4,797,273 A | 1/1989 | Linn et al. .................... 424/59 |
| 4,798,823 A | 1/1989 | Witzel .......................... 514/11 |
| 4,835,002 A | 5/1989 | Wolf et al. .................. 426/590 |
| 4,888,239 A | 12/1989 | Brox ....................... 428/402.2 |
| 4,914,188 A | 4/1990 | Dumont et al. ............. 530/317 |
| 4,963,367 A | 10/1990 | Ecanow ....................... 424/484 |
| 4,990,337 A | 2/1991 | Kurihara et al. |
| 4,996,193 A | 2/1991 | Hewitt et al. |
| 5,037,653 A | 8/1991 | Dawson ....................... 424/405 |
| 5,047,396 A | 9/1991 | Orban et al. .................. 514/11 |
| 5,154,754 A | 10/1992 | Damo et al. ............. 71/DIG. 1 |

(List continued on next page.)

FOREIGN PATENT DOCUMENTS

| AU | 10851/83 | 8/1983 |
|---|---|---|
| AU | 70043/87 | 10/1987 |
| BE | 895724 | 7/1983 |
| CA | 1209361 | 8/1986 |
| CH | 2461786 | 6/1983 |
| CH | 8634788 | 6/1983 |
| CH | 641356 | 2/1984 |
| DD | 295765 | 11/1991 |
| DE | 3315805 | 11/1984 |
| EP | 274431 | 7/1983 |
| EP | 135171 | 3/1985 |
| EP | 170623 | 2/1986 |
| EP | 211258 | 2/1987 |
| EP | 256856 | 2/1988 |
| EP | 314689 | 5/1989 |
| EP | 0 315 079 | 5/1989 |
| EP | 361928 | 4/1990 |
| EP | 365044 | 4/1990 |
| EP | 0 378 893 | 7/1990 |
| EP | 570829 | * 11/1993 |

(List continued on next page.)

OTHER PUBLICATIONS

Takada, et al., J. Pharmacobio. Dyn., vol. 11, pp. 80–87 (1988).
Ritschel, et al., Meth. Find. Exp. Clin. Pharmacol., vol. 11, pp. 281–287 (1989).
Tarr, et al., Pharmaceutical Research, vol. 6, No. 1, pp. 40–43 (1989).
Reymond, et al., Pharmaceutical Research, vol. 5, No. 10, pp. 677–679 (1988).
U.S. application No. 08/325254, Richter et al., filed Apr. 18, 1995.
95:225610K, Anon. (1981).
Anon., Research Disclosure 21143 (Nov. 1981).
Beyer et al., Pharmazie in unserer Zeit, vol. 12(2):55–60 (1983).
Bhargava et al., Pharmaceutical Technology, Mar. 1987.
Cavanak and Sucker, Prog. Allergy vol. 38:65–72 (1986).
Ekman, S., Lipids 22:657–663 (1987).
Ritschel, et al., Pharmaceutical Research vol. 5(10): Suppl. 108 PD 943 (1988).
Stupar et al., Goldschmidt Inforwist Essein. vol. 52: 22–28 (1982) translation.

(List continued on next page.)

*Primary Examiner*—Kevin E. Weddington
(74) *Attorney, Agent, or Firm*—Gabriel Lopez

(57) ABSTRACT

A pharmaceutical composition in the form of an emulsion preconcentrate for oral administration and containing a cyclosporin. The pharmaceutical composition has a carrier medium for the cyclosporin that contains a hydrophilic organic solvent; a mixed mono-, di-, and tri-glyceride or a transesterified and polyethoxylated vegetable oil; and a polyoxyethylene-sorbitan-fatty acid ester surfactant. The pharmaceutical composition provides high bioavailability and low inter- and intra-subject variability.

16 Claims, No Drawings

U.S. PATENT DOCUMENTS

| | | | |
|---|---|---|---|
| 5,206,219 A | 4/1993 | Desai | |
| 5,338,761 A | 8/1994 | Nakajima et al. | 514/772 |
| 5,342,625 A * | 8/1994 | Hauer et al. | 424/455 |
| 5,441,738 A | 8/1995 | Klein et al. | 424/195.1 |
| 5,504,068 A | 4/1996 | Komiya et al. | 514/11 |
| 5,525,590 A | 6/1996 | Bollinger et al. | |
| 5,639,724 A | 6/1997 | Cavanak | 514/11 |
| 5,756,450 A | 5/1998 | Hahn et al. | 514/9 |
| 5,866,159 A * | 2/1999 | Hauer et al. | 424/450 |
| 5,916,589 A * | 6/1999 | Hauer et al. | 424/450 |
| 5,962,014 A * | 10/1999 | Hauer et al. | 424/450 |
| 6,007,840 A * | 12/1999 | Hauer et al. | 424/450 |
| 6,024,978 A * | 2/2000 | Hauer et al. | 424/450 |
| 6,028,067 A * | 2/2000 | Hong et al. | 514/200 |

FOREIGN PATENT DOCUMENTS

| | | |
|---|---|---|
| FR | 2553661 | 4/1985 |
| FR | 2 642 650 | 8/1990 |
| GB | 616190 | 1/1949 |
| GB | 1171125 | 11/1969 |
| GB | 2 015 339 A | 9/1979 |
| GB | 2098865 | 12/1982 |
| GB | 2206119 | 12/1988 |
| GB | 2209671 | 5/1989 |
| GB | 2 211 408 | 7/1989 |
| GB | 2211848 | 7/1989 |
| GB | 2218334 | 11/1989 |
| GB | 2221157 | 1/1990 |
| GB | 2222770 | 3/1990 |
| GB | 2 224 205 A | 5/1990 |
| GB | 2228198 | 8/1990 |
| GB | 2230440 | 10/1990 |
| GB | 2257359 | 1/1993 |
| JP | 280435 | 4/1985 |
| JP | 61/249918 | 11/1986 |
| WO | 8602264 | 4/1986 |
| WO | 87/01035 | 2/1987 |
| WO | 88/00059 | 1/1988 |
| WO | 90/08537 | 8/1990 |
| WO | 91/08676 | 6/1991 |
| WO | WO 92/11860 | 7/1992 |
| WO | 93/09211 | 5/1993 |
| WO | 93/20833 | 10/1993 |

OTHER PUBLICATIONS

Takada, 87–024776/04 (Apr. 4, 1985).
Hahn, Biodegradable Tensides (1988) (translation).
Jayakrishnan, et al., J. Soc. Cosmet, Chem. 34:335–350 (1983).
Mizushima, 86–335072/51 (Jul. 26, 1985).
Mubarak, Development and Testing of New Microemulsions (1982) (translation).
Muller, et al., Pharm. Ind. 50 (11) 1301–1306 (1988) (translation).
Muller, et al., Pharm. Ind. 50(3): 370–375 (1988) (translation).
Pohler, Micro–Emulsion Gels Structural Investigations and Galenical Properties (1983) (translation).
Remington's Pharmaceutical Sciences (17th ed.) Microemulsions, Chapter 20, pp. 298–299 (1985).
Reymond et al., Pharmaceutical Research vol. 5(10): 673–676 (1988).
Reymond, In Vitro In Vivo Model for the Absorption of Cyclosporin A (1986) (translation).
Ritschel, et al., Meth Find Exp Clin Pharmacol, vol. 12, pp. 127–134 (1990).
W. A. Ritschel, Meth Find Exp Clin Pharmacol, vol. 13(3) pp. 205–220 (1991).
Takada et al., Int. of Pharmaceutics, vol. 44:107–116 (1988).
Takada et al., J. Pharmaceutical Research vol. 3(1):48–51 (1986).
Takada et al., J. Pharmacobio–Dyn. vol. 8:320–323 (1985).
Takada et al., J. Pharmacobio–Dyn. vol. 9:156–160 (1986).
Yanagawa et al., J. Microencapsulation 6(2): 161–164 (1989).
Ziegenmeyer, et al., Acta Pharmaceutical Technologica, vol. 26(4):273–275 (1980) (translation).
Ulman's Encyclopaedia of Industrial Pharmacy, vol. A9, pp. 298–299 and 308–311 (1987).
Carrigan et al., J. Pharm. Sci., vol. 62, pp. 1476–1479 (1973).
Frazer et al., J. Physiol., vol. 103, pp. 306–310 (1944).
Drewe et al., Br. J. Clin. Pharmac. vol. 33, pp. 39–43 (1992).
Charley, Helen. Food Science, 2nd edition, John Wiley & Sons (1982).
Derwent Abstract 89–229298/32.
Derwent Abstract 90–255218/34.
Derwent Abstract 86–335072.
Derwent Abstract 87–024776.
Derwent Abstract 1990–085699.
Derwent Abstract 1989–334771.
Derwent Abstract 1989–094742.
Derwent Abstract 92–216793/26.
Derwent Abstract 92–235168/29.
Derwent Abstract 84–069426/12.
The Merck Index, 9th Ed., Merck & Co., Inc., Rahway, NJ, p. 1017 (1976).

* cited by examiner

PHARMACEUTICAL COMPOSITIONS CONTAINING CYCLOSPORINS

Continuation of Ser. No. 09/444,974, Nov. 22, 1999 now abandoned, which is a continuation of Ser. No. 09/174,904, Oct. 19, 1998, abandoned, which is a continuation of Ser. No. 08/971,432, Nov. 17, 1997, abandoned, which is a continuation of Ser. No. 08/570,273, Dec. 11, 1995, abandoned, which is a continuation of Ser. No. 08/126,946, Sep. 24, 1993, abandoned.

This invention relates to galenic formulations which contain one or more members selected from the cyclosporin class.

Cyclosporins comprise a class of structurally distinct, cyclic, poly-N-methylated undecapeptides, generally possessing immunosuppressive, anti-inflammatory, anti-viral and/or anti-parasitic activity, each to a greater or lesser degree. The first of the cyclosporins to be identified was the fungal metabolite Cyclosporin A, or Ciclosporin, and its structure is given in The Merck Index, 11th Edition; Merck & Co., Inc.; Rahway, N.J., USA (1989) under listing 2759. Large numbers of other cyclosporins are also known and examples are disclosed in UK patent application No 2 222 770 A.

Cyclosporins are generally very insoluble in aqueous media. Consequently, severe difficulties have arisen in developing stable pharmaceutically acceptable formulations which allow delivery of the drug in sufficiently high concentrations to permit convenient use and which allow efficient and consistent absorption of the drug by the body. Problems also arise with regard to drug bioavailability and variability in patient dose response. Cyclosporins also have side effects at higher doses and therefore their concentration in the blood must be kept within certain therapeutic ranges. It is therefore desirable for the bioavailability of the cyclosporin drug to be as predictable and constant as possible.

In order to meet these and related difficulties, UK patent application 2 222 770 (the disclosure of which is incorporated by reference), discloses galenic formulations comprising a cyclosporin and which take the form of a microemulsion or microemulsion pre-concentrate. These formulations comprise a hydrophilic phase, a lipophilic phase and a surfactant. The following components for the hydrophilic phase are proposed: Transcutol, Glycofurol and 1,2-propylene glycol. Medium chain fatty acid triglycerides are disclosed as being suitable for the lipophilic phase. Reaction products of natural or hydrogenated vegetable oils and ethylene glycol are given as surfactants.

UK patent application 2 228 198 proposes an alternative means for meeting difficulties in relation to cyclosporin administration. Specifically it discloses oil based formulations in which the oily component comprises a combination of tri-glyceride and (i) glycerol partial esters or (ii) 1,2-propylene glycol complete or partial esters or (iii) sorbitol complete or partial esters. The products known and commercially available under the trade name MAISINE are proposed as suitable tri- and partial glyceride components. The disclosed compositions additionally comprise a surfactant component, for example Cremophor RH40. These may be preferably free of any hydrophilic components such as ethanol.

It has now surprisingly been found that simple, stable cyclosporin formulations that have improved bioavailability characteristics, reduced variability in inter- and intra-subject bioavailability parameters, are obtainable.

Accordingly this invention provides a pharmaceutical composition in the form of an emulsion preconcentrate and comprising a cyclosporin in a carrier medium, the carrier medium comprising: 1) a hydrophilic organic solvent, 2) (a) a mixed mono-, di-, and tri-glyceride or (b) a transesterified and polyethoxylated vegetable oil, and 3) a polyoxyethylene-sorbitan-fatty acid ester surfactant.

The pharmaceutical compositions are simple, stable, and provide surprisingly high bioavailabilities. For example, in clinical trials in which healthy volunteers each received three times 200 mg cyclosporin A in soft gelatin capsules under fasted and fed conditions, the pharmaceutical compositions resulted in at least a 150% increase in bioavailability as compared to the Cyclosporin market form which is disclosed in U.S. Pat. No. 4,388,307. Also, in the same trials, the relative bioavailability under fasted and fed conditions differed by less than 5%. This indicates very low inter-subject variability. Moreover intra-subject variability is reduced more than two fold. Hence the pharmaceutical compositions have very surprising properties which offer great advantages over the Cyclosporin market form.

The pharmaceutical composition is an emulsion preconcentrate; that is it has the characteristics of a stable emulsion preconcentrate system and spontaneously forms an emulsion in an aqueous medium, for example, in water or in the gastric juices after oral application. The emulsion formed is opaque, thermodynamically stable and contains dispersed droplets of a size greater than about 100 nm, more usually greater than about 200 nm. The pharmaceutical compositions are preferably emulsion preconcentrates of the type providing o/w (oil-in-water) emulsions.

The term "pharmaceutical composition" as used in this specification means compositions of which the individual components or ingredients are themselves pharmaceutically acceptable. For example, where oral administration is foreseen, the components are suitable or acceptable for oral application.

The cyclosporin may be any cyclosporin having pharmaceutical utility as, for example, an immunosuppressive agent, an anti-parasitic agent or an agent for the reversal of multi-drug resistance. In particular the cyclosporin may be Cyclosporin A (also known as and referred to as Ciclosporin), and Cyclosporin G.

Suitably the pharmaceutical composition comprises from about 1 or 2 to 30%, preferably from 5 to 25% (more preferably from 7.5 to 15%, for example about 10%) by weight of cyclosporin based on the total weight of the pharmaceutical composition.

The hydrophilic organic solvent preferably comprises pharmaceutically acceptable, hydrophilic organic solvents which are suitable for oral administration. Examples are Transcutol, Glycofurol, ethyl acetate, propylene glycol and lower alkanols, or mixtures thereof. Preferred solvents are 1,2-propylene glycol and mixtures of 1,2-propylene glycol and ethanol. If the component (2) is a mixed mono-, di- and tri-glyceride, 1,2-propylene glycol and mixtures of 1,2-propylene glycol and ethanol are particularly preferred.

Suitably the hydrophilic organic solvent is present in an amount of from 1.0 to 50% (preferably from 5 to 40%, more preferably from 10 to 35%, and even more preferably from about 15 to about 30%) by weight based on the total weight of the carrier medium.

When the hydrophilic organic solvent comprises a mixture of 1,2-propylene glycol and ethanol, the co-component, that is the ethanol, is suitably present in an amount of up to about 20% (preferably up to about 15%, more preferably from about 5 to 15% and even more preferably 5 to 10%) by weight based in the total weight of the pharmaceutical composition. Thus the co-component is suitably present in an amount of from about 25 to 85% by weight based on the total weight of the organic solvent (for example 1,2-propylene glycol plus ethanol). More preferably the co-component is present in an amount of from 50% to 85%, for example from 70 to 80% based on the total weight of the hydrophilic organic solvent.

If component (2) comprises mixed mono-, di-, and tri-glycerides, the mixed mono-, di-, and tri-glycerides preferably comprise a mixture of $C_{12-20}$ fatty acid mono-, di- and tri-glycerides. $C_{16-18}$ fatty acid mono-, di- and triglycerides are especially preferred. The fatty acid component of the mixed mono-, di- and tri-glycerides may comprise both saturated and unsaturated fatty acid residues. Preferably however the mixed glycerides are predominantly comprised of unsaturated fatty acid residues, in particular $C_{18}$ unsaturated fatty acid residues such as linolenic, linoleic and oleic acid residues. Suitably the mixed glycerides comprise at least 60%, preferably at least 75%, more preferably 85% or more by weight $C_{18}$ unsaturated fatty acid mono-, di- and tri-glycerides. Suitably the mixed glycerides comprise less than 20%, for example about 15% or 10% by weight, saturated fatty acid mono-, di- and tri-glycerides (for example palmitic and stearic acid mono-, di- and tri-glycerides).

The mixed mono-, di-, and tri-glycerides are preferably predominantly comprised of mono- and di-glycerides. For example they comprise at least 50%, more preferably at least 70% (for example 75%, 80%, or 85% by weight) mono- and di-glycerides, based on the total weight of component (2)(a).

The mixed mono-, di-, and tri-glycerides suitably comprise from about 25 to about 50% (preferably from about 30 to about 40%, and more preferably about 35 to 40%) monoglycerides, based on the total weight of component (2)(a).

The mixed mono-, di-, and tri-glycerides suitably comprise from about 30 to about 60% (preferably from about 40 to about 55%, and more preferably about 45 to 50%) di-glycerides, based on the total weight of component (2)(a).

The mixed mono-, di-, and tri-glycerides suitably comprise at least 5% (preferably from about 7.5 to about 20%, and more preferably 9 to 15%) by weight of triglycerides, based on the total weight of component (2)(a).

The mixed mono-, di-, and tri-glycerides may be prepared by admixing individual mono-, di- or tri-glycerides in appropriate relative proportion. Conveniently however the mixed glycerides comprise transesterification products of vegetable oils, for example almond oil, ground nut oil, olive oil, peach oil, palm oil, soybean oil, corn oil, sunflower oil or safflower oil, with glycerol. Preferably the vegetable oil is corn oil. Also mixtures of the oils may be transesterified with glycerol.

The transesterification products are generally obtained by heating the selected vegetable oil with glycerol to effect trans-esterification or glycerolysis. This may be carried out at high temperature in the presence of an appropriate catalyst, under an inert atmosphere and with continuous agitation. In addition to the mono-, di- and tri-glyceride components, the transesterification products also generally comprise minor amounts of free glycerol. However the amount of free glycerol in the mixed mono-, di-, and tri-glycerides is preferably less than 10%, more preferably less than 5%, most preferably about 1 to 2% by weight, based on the total weight of component (2)(*a*).

Preferably some of the glycerol is first removed (for example by distillation) to give a "substantially glycerol free batch", when soft gelatine capsules are to be made.

Trans-esterification products of corn oil and glycerol provide particularly suitable mixed mono-, di-, and tri-glycerides. An example of a suitable mixed glyceride product is the trans-esterification product commercially available under the trade name MAISINE. This product is comprised predominantly of linoleic and oleic acid mono-, di- and tri-glycerides together with minor amounts of palmitic and stearic acid mono-, di- and tri-glycerides (corn oil itself being comprised of about 56% by weight linoleic acid, 30% oleic acid, about 10% palmitic and about 3% stearic acid constituents). The physical characteristics of MAISINE [available from the company Etablissements Gattefossé, of 36, Chemin de Genas, P.O. Box 603, 69804 Saint-Priest, Cedex (France)] are: up to 10% (typically 3.9 to 4.9% or, in "substantially glycerol free" batches, about 0.2%) free glycerol; about 35% (typically 30 to 40% or, in "substantially glycerol free" batches, about 32 to 36%, for example about 36%) mono-glycerides; about 50% (or, in "substantially glycerol free" batches about 46 to 48%) di-glycerides; about 10% (or, in "substantially glycerol free" batches, about 12 to 15%) tri-glycerides; and about 1% free oleic acid.

Further physical characteristics for MAISINE are: an acid value of maximum about 2, an iodine no. of about 85 to 105, a saponification no. of about 150 to 175 (Fiedler "Lexikon der Hilfsstoffe", 3rd revised and expanded edition (1989) Vol. 2, p.768). The fatty acid content for MAISINE is typically: about 11% palmitic acid; about 2.5% stearic acid; about 29% oleic acid; about 56% linoleic acid; and 1.5% other acids.

It is especially preferred that the mixed mono-, di-, and tri-glycerides are clear and remain clear for more than 20 days upon storage at temperatures of 20° C. to 25° C. Also, a sample of the mixed mono-, di-, and tri-glycerides, which has been kept in a refrigerator at about between 2 and 8° C. for 24 hours and then held at room temperature for 1 hour, should be clear.

Preferably the mono-, di-, tri-glycerides have a low saturated fatty acid content. Mixed mono-, di-, tri-glycerides meeting these requirements may be obtained from commercially available products by separation techniques as known in the art (for example freezing procedures coupled with separation techniques such as centrifugation) to remove the saturated fatty acid components and enhance the unsaturated fatty acid component content. Typically the total saturated fatty acid component content will be less than 15%, (for example <10%, or <5%) by weight based on the total weight of the component (2)(a).

A reduction of the content of saturated fatty acid component in the mono-glyceride fraction may be observed after being subjected to the separation technique. A suitable process is described in WO 93/09211.

Hence the mixed mono-, di-, tri-glycerides preferably contain lesser quantities of saturated fatty acids (e.g. palmitic and stearic acids) and relatively greater quantities of unsaturated fatty acids (e.g. oleic and linoleic acids) than the starting material.

A suitable example of a mixed mono-, di-, tri-glyceride product containing lesser quantities of saturated fatty acids contains: 32 to 36% mono-glycerides, 45 to 55% di-glycerides and 12 to 20% tri-glycerides, by weight based on the total weight of the lipophilic phase. Further characteristics include the following:

| | |
|---|---|
| Fatty acid content | Methyl linoleate 53 to 63%, |
| (as determined as the methyl ester by | Methyl oleate 24 to 34%, |
| chromatography) | Methyl linolenate 0 to 3% |
| | Methyl arachate 0 to 3%, |
| | Methyl palmitate 6 to 12%, |
| | Methyl stearate 1 to 3% |
| Relative Density | 0.94 to 0.96 |
| Hydroxyl Value | 140 to 210 |
| Iodine Value | 110 to 20 |
| Peroxide Value | <4.0 |
| Free Glycerol | <1.0 |

| | |
|---|---|
| Saponification no | about 150 to 185 |
| Acid value | max. about 2 |

Mixed mono-, di-, tri-glycerides complying with these characteristics are referred to in this specification as "refined glycerol-transesterified corn oils". The "refined glycerol-transesterified corn oils" have the advantage of remaining stable for a long time.

If components (2) comprises a transesterified and polyethoxylated vegetable oil, it preferably comprises transesterification products which are formed by transesterifying a vegetable oil triglyceride with a polyethylene glycol. Preferred transesterified and polyethoxylated vegetable oils are obtainable by transesterification of triglycerides from kernel oil, almond oil, ground nut oil, olive oil, soybean oil, maize oil, sunflower oil, safflower oil and/or palm oil, with one molar equivalent of a polyethylene glycol that has a molar weight between 200 and 800. These transesterified and polyethoxylated vegetable oils are available from GATTEFOSSÉ, Saint-Priest Cedex, France, under the trade name LABRAFIL (Fiedler loc cit, Vol. 2, page 707). A preferred transesterified and polyethoxylated vegetable oil is LABRAFIL 2125 CS (oleic acid linoleic acid glyceride from maize oil) having an acid number of 2, a saponification number of 155 to 175 and an iodine number of 90 to 110. Another example is LABRAFIL M 1944 CS (obtained from kernel oil and having an acid number of about 2, a saponification number of 145 to 175 and an iodine number of 60 to 90). LABRAFIL M 2130 CS (which is a transesterification product of a $C_{12-18}$ glyceride and polyethylene glycol and which has a melting point of about 35 to 40° C., an acid number of less than about 2, a saponification number of 185 to 200 and an iodine number of less than about 3) may also be used. The preferred transesterified ethoxylated vegetable oil is LABRAFIL M 2125 CS.

The transesterification products are generally obtained by heating the selected vegetable oil with polyethylene glycol to effect transesterification. This is done at high temperature in the presence of an appropriate catalyst under an inert atmosphere with continuous agitation. This process is described in U.S. Pat. No. 3,288,824.

The transesterified and polyethoxylated vegetable oil may also comprise esters of saturated or unsaturated $C_{12-20}$ fatty acids with glycerol or propylene glycol, for example glycerol monooleate. Products of this type are known and commercially available.

Suitably component (2) is present in the pharmaceutical compositions in an amount of from 5 to 65%, preferably from 15 to 45%, more preferably from 20 to 40%, and even more preferably from about 25 to about 40%, based on the total weight of the carrier medium.

The polyoxyethylene-sorbitan-fatty acid ester surfactant preferably has an HLB of at least 10. Examples of suitable polyoxyethylene-sorbitan-fatty acid ester surfactants are mono- and tri-lauryl, palmityl, stearyl and oleyl esters such as those known and commercially available under the trade name TWEEN (Fiedler, loc.cit. p.1300–1304). Examples include the TWEEN 20 [polyoxyethylene(20)sorbitanmonolaurate],
21 [polyoxyethylene(4)sorbitanmonolaurate],
40 [polyoxyethylene(20)sorbitanmonopalmitate],
60 [polyoxyethylene(20)sorbitanmonostearate],
65 [polyoxyethylene(20)sorbitantristearate],
80 [polyoxyethylene(20)sorbitanmonooleate],
85 [polyoxyethylene(20)sorbitantrioleate].

Especially preferred TWEEN 20 and TWEEN 80.

Suitably the polyoxyethylene-sorbitan-fatty acid ester is present in the pharmaceutical compositions in an amount of from 25 to 75% (preferably from 30 to 60%, more preferably from about 30 or 40%) based on the total weight of the carrier medium.

The pharmaceutical composition may further include (4) water, in which case the pharmaceutical composition is in the form of a stable emulsion.

The pharmaceutical composition may also include further additives or ingredients, for example antioxidants (such as ascorbyl palmitate, butyl hydroxy anisole (BHA), butyl hydroxy toluene (BHT) and tocopherols) and/or preserving agents. These additives or ingredients may comprise about 0.05 to 1% by weight of the total weight of the pharmaceutical composition. The pharmaceutical composition may also include sweetening or flavoring agents in an amount of up to about 2.5 or 5% by weight based on the total weight of the pharmaceutical composition. Preferably the antioxidant is α-tocopherol (vitamin E).

The pharmaceutical composition has been found to exhibit especially advantageous properties when administered orally in terms of both the consistency and high level of bioavailability achieved as indicated in standard bioavailability tests and clinical trials. Hence the pharmaceutical composition provides an improved oral administration form for cyclosporins (e.g. Ciclosporin) as it exhibits absence of significant food interaction, which has been observed with the commercially available oral form of Ciclosporin, especially with fat, rich food. Moreover, inter-subject and intra-subject variability of pharmacokinetic parameters are significantly lower than with the commercially available oral form of Ciclosporin. Thus the pharmacokinetic parameters (for example absorption and blood levels), become surprisingly more predictable and this reduces problems which have occurred previously with erratic absorption of Ciclosporin.

Additionally the pharmaceutical composition exhibits improved bioavailability in patients having malabsorption, for example liver transplantation patients or pediatric patients. Further the pharmaceutical composition is compatible with tenside materials, for example bile salts, present in the gastro-intestinal tract. That is, the pharmaceutical composition is fully dispersible in aqueous systems comprising such natural tensides and is thus capable of providing emulsion systems in situ which are stable and do not exhibit precipitation of the active ingredient or other disruption of fine particulate structure. The function of the pharmaceutical composition upon oral administration remains substantially independent of and/or unimpaired by the relative presence or absence of bile salts at any particular time or for any given individual.

The pharmaceutical composition is preferably compounded into unit dosage form, for example by filling it into orally administrable capsule shells (for example soft or hard gelatine capsule shells) but, if desired, may be in drink solution form. Where the pharmaceutical composition is in unit dosage form, each unit dosage suitably contains between 10 and 200 mg cyclosporin, more suitably between 10 and 150 mg, for example 15, 20, 25, 50 or 100 mg cyclosporin. Such unit dosage forms are suitable for administration 1×, 2×, 3× and up to 5× daily (for example, depending on the particular purpose of therapy, the phase of therapy, etc.).

The utility of the pharmaceutical composition can be observed in standard clinical tests in, for example, known indications of cyclosporins at dosages giving equivalent blood levels of cyclosporins; for example using dosages in the range of 25 mg to 1000 mg of cyclosporin per day for a 75 kilogram adult and in standard animal models. The increased bioavailability of the active ingredient provided by the compositions can be observed in standard animal tests and in clinical trials, for example as set out in Examples 4 and 5.

The optimal dosage of cyclosporin to be administered to a particular patient must be considered carefully by the treating physician as individual response to and metabolism of the cyclosporin may vary. It may be advisable to monitor the blood serum levels of the cyclosporin by radioimmunoassay, monoclonal antibody assay, or other appropriate conventional means. Dosages of the cyclosporin will generally range from 25 mg to 1000 mg per day for a 75 kilogram adult, preferably 50 mg to 500 mg. Satisfactory results are obtained by administering capsules containing 50 mg or 100 mg cyclosporin in amounts to make up a dose as needed.

In another aspect the invention also provides a process for the production of a pharmaceutical composition as defined above, which process comprises admixing a cyclosporin; an organic solvent; a mixed mono-, di-, and tri-glyceride or a transesterified and polyethoxylated vegetable oil; and a polyoxyethylene-sorbitan-fatty acid ester. If required, the obtained pharmaceutical composition may be compounded into unit dosage form.

In a more particular embodiment, the components are admixed such that an emulsion preconcentrate and, when required, combining the obtained pharmaceutical composition with sufficient water or sufficient of an aqueous solvent medium such that an emulsion is obtained.

The following examples are illustrative of the pharmaceutical composition, in unit dosage form, suitable for use, for example in the prevention of transplant rejection or for the treatment of autoimmune disease, on administration of from 1 to 5 unit dosages/day. The examples are described with particular reference to Ciclosporin and [O-(2-hydroxyethyl)-(D)-Ser]$^8$-Ciclosporin (referred to as Compound Z in this specification). However equivalent pharmaceutical compositions may be obtained employing any other cyclosporin.

EXAMPLE 1
Preparation of "Refined Glycerol-Transesterified Corn Oil"

Substantially-glycerol free, glycerol-transesterified corn oil (if necessary after heating to give a clear mixture) is slowly cooled to a temperature of +20° C. and kept at this temperature for one night. The corn oil is centrifuged at an acceleration of 12 000 G and at a flow rate of 103 kg/h in a continuous flow centrifuge to give a liquid phase (62 kg/h) and a sediment-containing phase (41 kg/h). The liquid phase is slowly cooled to +8° C. and kept at this temperature for one night. The liquid phase is then centrifuged at an acceleration of 12 000 G and at a flow rate of 112 kg/h to give a liquid phase (76.2 kg/h) and a sediment-containing phase (35.8 kg/h). The liquid phase is "refined glycerol-transesterified corn oil". Alternatively an improved product may be obtained by effecting the centrifugation in three steps, e.g. at +20° C., +10° C. and +5° C.

The process is characterised by a slight percentage reduction in the mono-glyceride component in the refined glycerol transesterified corn oil as compared to the starting material (e.g. 35.6% compared to 38.3%).

A typical analytical comparison between the sediment and clear solution is as follows:

| Compound | Sediment (%) | Clear Solution (%) |
|---|---|---|
| Mono palmitate | 19.1 | 3.4 |
| Mono linoleate + Mono oleate | 23.4 | 27.0 |
| Mono stearate | 5.7 | <2 |
| Dilinoleate + Dioleate | 35.4 | 44.7 |
| Other di-glycerides | 7.7 | 10.4 |
| Tri-glycerides | 8.7 | 12.5 |

In a variant of this refining procedure, similar "refined glycerol-transesterified corn oil" compositions may be obtained by heating the starting material to +80° C. for one hour under nitrogen. Then the heated material is cooled down to +16° C., while agitated slightly, using a 1° C. difference between temperature of the material and temperature of the cooling fluid. The cooled material is maintained at +16° C. for about 12 hours, while agitated slightly, and then cooled down to about +8° C. Precipitate is then removed by means of a band filter under vacuum.

In a further variant, similar "refined glycerol-transesterified corn oil" compositions may be obtained by heating the starting material to +75° C. under nitrogen and then cooling it down to +8° C. within a period of 5 to 6 hours.

In yet a further variant, similar "refined glycerol-transesterified corn oil" compositions may be obtained by heating the starting material to +80° C. for 1 hour and then cooling it down to +8° C. using a stepwise cooling procedure. The cooling procedure comprises: cooling to +25° C. in 1 hour, maintaining at +25° C. for 8 hours, cooling to +20° C. in 0.5 hours, maintaining at +20° C. for 1 hour, cooling to +15° C. in 0.5 hours, maintaining at +15° C. for 1 hour, cooling to +10° C. in 0.5 hours, maintaining at +10° C. for 1 hour, cooling to +8° C. in 0.5 hours, staying at 8° C. for 2 hours, and filtering the batch through a 0.5 μm mesh filter under a pressure of 0.5 bars.

A typical refined product obtained from these procedures contains the following:

| Components | |
|---|---|
| Glycerides: | |
| mono | 33.3 |
| di | 52.1 |
| tri | 14.6 |
| Fatty acids: | |
| palmitic acid (C16) | 7.8 |
| stearic acid (C18) | 1.7 |
| oleic acid (C18:1) | 31.6 |
| linoleic acid (C18:2) | 57.7 |
| Glycerol content | <1% |

EXAMPLE 2
Preparation of Oral Unit Dosage Forms

| COMPONENT | Ex 2(a)/ mg | Ex 2(b)/ mg | Ex 2(c)/ mg | Ex 2(d)/ mg | Ex 2(e)/ mg |
|---|---|---|---|---|---|
| Ciclosporin | 50 | 100 | 50 | 50 | 100 |
| 1,2-propylene glycol | 37 | 38 | 80 | 19 | 160 |
| ethanol | 75 | 135 | 50 | 67.5 | 100 |

-continued

| COMPONENT | Ex 2(a)/ mg | Ex 2(b)/ mg | Ex 2(c)/ mg | Ex 2(d)/ mg | Ex 2(e)/ mg |
|---|---|---|---|---|---|
| MAISINE | 113 | — | — | — | — |
| LABRAFIL 2125 CS | — | 344 | 40 | 172 | 80 |
| TWEEN 80 | 225 | 383 | 280 | 191.5 | 560 |
| Total per capsule | 500 | 1000 | 500 | 500 | 1000 |

The cyclosporin is dissolved in the 1,2-propylene glycol and ethanol with stirring at room temperature. MAISINE or LABRAFIL 2125 CS and TWEEN 80 are added to the obtained solution again with stirring. The obtained mixture is filled into hard or soft gelatine capsules. The hard gelatin capsules may be sealed, for example using the Quali-Seal technique.

Instead of filling the mixture in the indicated amount into unit dosage forms (i.e. hard gelatine capsules or soft gelatine capsules), a storage mixture may be prepared by combining the indicated components in the indicated ratios. Such storage mixtures may serve for exactly administering the required dosage to a patient, being in need of dosage other than simple multiples of the unit dosage form.

EXAMPLE 3
Preparation of Oral Unit Dosage Forms for Compound Z

| COMPONENT | Ex 3(a)/ mg | Ex 3(b)/ mg | Ex 3(c)/ mg |
|---|---|---|---|
| Compound Z | 50 | 50 | 50 |
| 1,2-propylene glycol | 100 | 112.5 | 115 |
| MAISINE | 175 | — | — |
| LABRAFIL 2125 CS | — | 90 | 115 |
| TWEEN 80 | 175 | 247.5 | 345 |
| Total per capsule | 500 | 500 | 625 |

The cyclosporin is dissolved in the 1,2-propylene glycol with stirring at room temperature. The MAISINE or LABRAFIL 2125 CS and Tween 80 are added to the obtained solution again with stirring. The obtained mixture is filled into hard or soft gelatine capsules. The hard gelatin capsules may be sealed, for example using the Quali-Seal technique.

Instead of filling the mixture in the indicated amount into unit dosage forms (i.e. hard gelatine capsules or soft gelatine capsules), a storage mixture may be prepared by combining the indicated components in the indicated ratios. Such storage mixtures may serve for exactly administering the required dosage to a patient, being in need of dosage other than simple multiples of the unit dosage form.

EXAMPLE 4
Bioavailability in Dogs

The biopharmaceutical properties are tested using the pharmaceutical composition in the form of unit dosage, gelatine capsules containing Ciclosporin or Compound Z. The pharmaceutical compositions are tested by orally administering the forms to 8 male beagle dogs in a cross-over design. The pharmacokinetic profile of Ciclosporin or Compound Z is determined in whole blood over 24 hours. The areas under the curve of the blood concentration versus time curves (AUC), $C_{max}$ and $T_{max}$ are determined.
Forms: A dose 50 mg Ciclosporin/dog using the forms of examples 2(a), 2(c), 2(d), 3(a), 3(b), 3(c).

Drug administration:
8 male beagle dogs weighing around 12 kg are used. Twenty hours before the drug administration, food is withdrawn but the animals are allowed free access to water until the beginning of the experiment. The dosage forms are administered by gavage to the animals, early in the morning (approx. 8.00 am), and are followed by 20 ml NaCl 0.9% solution. Three hours after the administration, the animals are again allowed free access to water and food. A one week wash-out period is necessary between 2 administrations to the same animal.

Blood sampling:
Blood samples of 2 ml (or 5 ml for the blank sample) are taken from the vena cephalica (forearm) with a sterile needle (diameter about 1.2 mm) and collected into 5 ml plastic tubes containing EDTA at -15 min, 30 min, 1 hour, 1.5 hours, 2 hours, 3 hours, 4 hours, 6 hours, 8 hours, 12 hours and 24 hours after the oral administration of the drug. The blood samples are stored at about -18° C. until drug assay. The blood samples are analyzed by radioimmunoassays (RIA). The median blood concentrations of Ciclosporin or Compound Z in dogs are plotted. The areas under the blood drug concentration versus time curves (AUC) are calculated using the trapezoidal rule. An analysis of variance (CV) is performed and the mean AUCs, $C_{max}$ and $T_{max}$ are compared statistically by the Tukey test. The results obtained are shown in the following table.

| Composition | $AUC_{0-24 h}$ Mean [ng.h/ml] | CV [%] | $C_{max}$ Mean [ng/ml] | CV [%] | $T_{max}$ Mean [h] | CV [%] |
|---|---|---|---|---|---|---|
| Ex 2(a) | 4220 | 13 | 814 | 15 | 0.9 | 26 |
| Ex 3(a) | 9857 | 25 | 1545 | 14 | 1.3 | 61 |
| Ex 2(c) | 3459 | 23 | 806 | 15 | 0.8 | 36 |
| Ex 2(d) | 4065 | 21 | 884 | 31 | 0.9 | 40 |
| Ex 3(b) | 8767 | 29 | 1146 | 23 | 1.3 | 30 |
| Ex 3(c) | 11558 | 23 | 1729 | 18 | 1.1 | 21 |

The behaviour and body weight of the animals are monitored during the study. No body weight loss or abnormal behaviour can be detected. The compositions have a therapeutically effective bioavailability.

EXAMPLE 5
Clinical Trial

The pharmaceutical properties of the pharmaceutical composition in humans are compared to those of Ciclosporin market form in a human trial. The pharmaceutical compositions are tested by orally administering the forms to 18 healthy volunteers in a cross-over design, under fasted and fed conditions. The pharmacokinetic profile of Ciclosporin is determined in whole blood over 24 hours using a specific monoclonal antibody. The areas under the curve of the blood concentration versus time curves (AUC), $C_{max}$ and $T_{max}$ are determined.

Three times 200 mg of Ciclosporin, in a form corresponding to the form of example 2a, is administered orally under fasted and fed conditions. For comparison, three times 200 mg of Ciclosporin, in the form of the Ciclosporin market form, is administered orally under fasted conditions. Blood samples of 2 ml (or 5 ml for the blank sample) are taken with a sterile needle and collected into 5 ml plastic tubes containing EDTA at −15 min, 30 min, 1 hour, 1.5 hours, 2 hours, 3 hours, 4 hours, 6 hours, 8 hours, 12 hours and 24 hours after the oral administration of the drug. The blood samples are stored at about −18° C. until drug assay. The blood samples are analyzed by radioimmunoassay (RIA) using a specific monoclonal antibody. The median blood concentrations of Ciclosporin are plotted. The areas under the blood drug concentration versus time curves (AUC) are calculated using the trapezoidal rule. An analysis of variance (CV) is performed and the mean AUCs, $C_{max}$ and $T_{max}$ are compared statistically by the Tukey test. The results obtained are shown in the following table.

| Composition | $AUC_{0-24\,h}$ Mean [ng.h/ml] | CV [%] | $C_{max}$ Mean [ng/ml] | CV [%] | $T_{max}$ Mean [h] | CV [%] |
|---|---|---|---|---|---|---|
| Ex 2a (fasted) | 4013 | 16 | 964 | 20 | 1.5 | 24 |
| Ex 2a (fed) | 4066 | 18 | 918 | 33 | 1.7 | 37 |
| Market (fasted) | 2958 | 35 | 637 | 41 | 2.3 | 52 |

Also the relative bioavailabilities are:
Example 2a (fasted): 151
Example 2a (fed): 159
Market form (fasted): 100

The results indicate that intra-subject variability in blood concentration is reduced more than two fold with the formulation of example 2a. Also the effect of food intake on bioavailability is small. Further, the ratio $C_{max}$/AUC (which gives an indication of rate of absorption) is up to 30% higher with the formulation of example 1. Moveover, the extent of absorption is up to twice greater, although on average 1.5 times, with the formulation of example 1. Consequently the pharmaceutical compositions have much better pharmacokinetic properties than the market form.

What is claimed is:

1. A pharmaceutical composition in the form of an emulsion preconcentrate and comprising a cyclosporin in a carrier medium, the carrier medium comprising: 1) a hydrophilic organic solvent, 2) (a) a mixed mono-, di-, and tri-glyceride or (b) a transesterified and polyethoxylated vegetable oil, and 3) a polyoxyethylene-sorbitan-fatty acid ester surfactant.

2. A composition according to claim 1 in which the hydrophilic organic solvent is selected from 1,2-propylene glycol and mixtures of 1,2-propylene glycol and ethanol.

3. A composition according to claim 2 in which the hydrophilic organic solvent comprises a mixture of 1,2-propylene glycol and ethanol; the ethanol comprising 25 to 85% by weight of the organic solvent.

4. A composition according to claim 1 in which component (2) is a mixed mono-, di-, and tri-glyceride comprising a trans-esterification product of a vegetable oil.

5. A composition according to claim 4 in which the mixed mono-, di- and tri-glycerides comprise at least 60% by weight $C_{18}$ unsaturated fatty acid mono-, di- and tri-glycerides and less than 20% by weight, saturated fatty acid mono-, di- and tri-glycerides.

6. A composition according to claim 4 in which the mixed mono-, di-, and tri-glycerides at least 70% mono- and di-glycerides, based on the total weight of component (2)(a).

7. A composition according to claim 6 in which the mixed mono-, di-, and tri-glycerides comprise from about 30 to about 40% by weight monoglycerides, from about 40 to about 55% by weight di-glycerides, from about 7.5 to about 20% by weight of triglycerides, and less than about 10% by weight free glycerol, based on the total weight of component (2)(a).

8. A composition according to claim 1 in which component (3) has an HLB value of at least 10.

9. A composition according to claim 8 in which component (3) is a polyoxyethylene(20)sorbitanmonooleate.

10. A pharmaceutical composition in the form of an emulsion preconcentrate and comprising from about 7.5 to about 15% by weight of a cyclosporin in a carrier medium, the carrier medium comprising: 1) about 15 to about 30% by weight of the carrier medium of a mixture of 1,2-propylene glycol and ethanol, 2) about 20 to 35% by weight of the carrier medium of a mixed mono-, di-, and tri-glyceride comprising about 0.2% free glycerol; about 32 to 36% mono-glycerides; about 46 to 48% di-glycerides; about 12 to 15% tri-glycerides; and about 1% free oleic acid, based on the weight of component (2), and 3) from about 30 to about 60% by weight of the carrier medium of a polyoxyethylene-sorbitan-fatty acid ester surfactant.

11. A composition according to claim 10 in which component (3) is a polyoxyethylene(20)sorbitanmonooleate.

12. A composition according to claim 1 in unit dosage form.

13. A composition according to claim 10 in unit dosage form.

14. A composition according to claim 1 further comprising an aqueous phase to form an emulsion.

15. A composition according to claim 10 further comprising an aqueous phase to form an emulsion.

16. A process for the production of a pharmaceutical composition as defined in claim 1, which process comprises admixing a cyclosporin; an organic solvent; a mixed mono-, di-, and tri-glyceride or a transesterified and polyethoxylated vegetable oil; and a polyoxyethylene-sorbitan-fatty acid ester.

* * * * *